May 22, 1973 P. R. BOSLEY Plant Pat. 3,339
PIERIS JAPONICA
Filed April 26, 1971
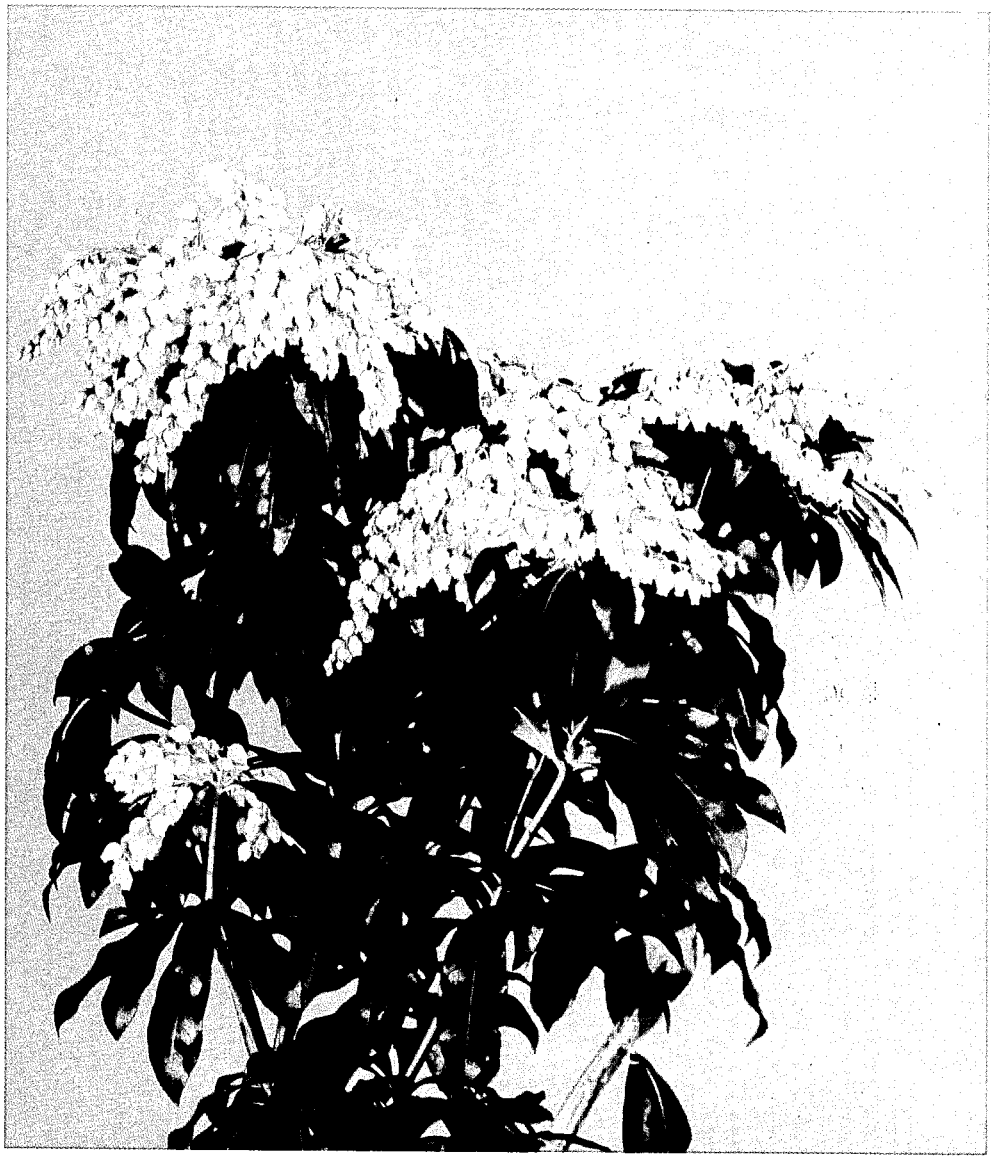

United States Patent Office

Plant Pat. 3,339
Patented May 22, 1973

3,339
*PIERIS JAPONICA*

Paul R. Bosley, 9579 Mentor Ave., Mentor, Ohio 44060

Filed Apr. 26, 1971, Ser. No. 137,720
Int. Cl. A01h *5/00*
U.S. Cl. Plt.—54 1 Claim This invention comprises a new and distinct variety of *Pieris japonica*, commonly known as Andromeda. The *Pieris japonica* of the invention is the result of a sport which was taken from a parent plant which has distinct foliage and hardiness characteristics.

The sport was discovered by me in the spring of 1967 in a cultivated area of my nursery located at 9579 Mentor Avenue, Mentor, Ohio, at which time it was apparent that this sport had desirable novel characteristics that should be preserved. This discovery followed a winter that was very hard on all broad leafed evergreens and an entire field of *Pieris japonica* was brown and unsaleable, except for this one particular plant that looked as fresh and green as it did throughout the previous summer. The winter of 1967–68 was equally hard on this field of Pieris, but this particular plant came through the winter with perfect color while the balance of the field was again burned so that the plants were completely unsaleable. The same condition of burning occurred in the winter of 1968–69, and again this one plant had the characteristic of remaining fresh and green while all the Pieris plants in the surrounding areas were again all brown and rendered unsaleable. Cuttings were made by me first in the spring of 1968 from the original plant and also in the subsequent propagating seasons thereafter. The same characteristic has been maintained to date by the said asexual propagation from this original plant.

The accompanying illustration shows one of the plants in bloom.

The following is a detailed description of the plant and its flowers:

Foliage: The foliage of this sport is deeper green in color and is noticeably glossier than *Pieris japonica* and in addition has a very interesting wavy characteristic that identifies it in the middle of the summer when the plants are in a succulent growing condition.

Flowers: The flowers are white and identical with those of *Pieris japonica* and of the same general size and structure.

Characteristics of growth and blooming: The plant habit and time of blooming is the same, namely in the spring, as that of *Pieris japonica*. This new variety blooms very heavily and with good full racemes of flowers.

I claim:

1. The new and distinct variety of *Pieris japonica* plant, substantially as herein described, characterized particularly by its ability to stay green under adverse conditions and not winter burn as *Pieris japonica* will often do, and having a glossier and wavy foliage than other known *Pieris japonica*.

No references cited.

ROBERT E. BAGWILL, Primary Examiner